United States Patent [19]
Kase et al.

[11] Patent Number: 4,692,310
[45] Date of Patent: Sep. 8, 1987

[54] SUBSTANCE K-259-2 AND A PROCESS FOR PRODUCING THE SAME

[75] Inventors: Hiroshi Kase, Koganei, Japan; Yuzuru Matsuda, Rockville, Md.; Isao Kawamoto, Hiratsuka, Japan; Kozo Asano, Machida, Japan; Kunikatsu Shirahata, Komae, Japan; Tohru Yasuzawa, Machida, Japan; Koji Yamada, Machida, Japan

[73] Assignee: Kyowa Hakko Kogyo Kabushiki Kaisha, Japan

[21] Appl. No.: 852,590

[22] Filed: Apr. 16, 1986

Related U.S. Application Data

[63] Continuation-in-part of Ser. No. 771,530, Aug. 30, 1985, abandoned.

[30] Foreign Application Priority Data

Sep. 3, 1984 [JP] Japan ................................ 59-184320

[51] Int. Cl.$^4$ .......................... A61K 35/74; C12P 1/06
[52] U.S. Cl. ..................................... 424/122; 435/169
[58] Field of Search ......................... 424/122; 435/169

[56] References Cited

PUBLICATIONS

Tawaka et al., J of Antibiotics, vol. XXXV, No. 2, pp. 151-156, (Feb. 1982).
Yoshida et al., J of Antibiotics, vol. XXXV, No. 2, pp. 157-163, (Feb. 1982).

Primary Examiner—Jerome D. Goldberg
Attorney, Agent, or Firm—Wolder, Gross & Yavner

[57] ABSTRACT

A new substance K-259-2 having a molecular formula of $C_{21}H_{18}O_7$, a molecular weight of 382 and an elemental analysis (%) of H: 4.50, C: 65.53 and N: 0. This substance is of interest in providing a new vasodilating agent in view of its ability to dilate the blood vessel, particularly the artery, of mammals. This substance may be obtained by fermentation of a microorganism Micromonospora sp. K-259 (FERM BP 569).

5 Claims, 2 Drawing Figures

SUBSTANCE K-259-2 AND A PROCESS FOR PRODUCING THE SAME

RELATED APPLICATION

This application is a continuation-in-part of U.S. patent application Ser. No. 771,530 filed on Aug. 30, 1985, which is now abandoned.

BACKGROUND OF THE INVENTION

The present invention relates broadly to a physiologically active substance of microorganism origin and more particularly to a substance capable of dilating the blood vessel of humans and animals. The present invention further relates to a process for the preparation of such a new substance.

A vasodilator is a substance capable of dilating the blood vessel, particularly the artery, enhancing the function of the peripheral blood vessel, particularly the peripheral artery and/or decreasing the overall blood pressure. It is useful, for example, for treating and curing high blood pressure, angina pectoris, the obstruction of peripheral artery, cardiac insufficiency and the like. Substances of microorganism origin which may be used as vasodilator are also known, for example, with reference to J. Antibiotics., 35, 151–156 (1982) and ibid., 35, 157–163 (1982) wherein WS-1228 substances are produced from *Streptomyces aureofaciens.*

Meanwhile, for example, antibiotics originating from the microorganisms of the genus Micromonospora are also known. However, a substance originating from microorganism of this genus and capable of dilating the blood vessel, particularly the arteries of humans and animals has not been reported in the art.

The present invention is based upon the discovery that a substance isolated from the cultured broth of a microorganism of the genus Micromonospora, is capable of effectively dilating the blood vessels, particularly the arteries of mammals.

Therefore, the present invention is directed to providing a new substance, designated as K-259-2, capable of dilating the blood vessel, particularly the artery of mammals. The present invention is of interest as a new vasodilator.

SUMMARY OF THE INVENTION

According to one feature of the present invention, there is provided a new substance designated as K-259-2 having the following physico-chemical characteristics:

(1) Nature: reddish needle crystal. Alkaline substance.

(2) Melting point: 140°–145° C. (decomp.). Becomes brownish at a temperature of more than about 140° C. Melting point indefinite.

(3) Specific rotation: $[\alpha]_D^{20}=0°$ (c=0.33, $CH_3OH$).

(4) Solubility: Readily soluble in acetic acid, soluble in methanol and water, and hardly soluble in chloroform, ethyl acetate, acetone and ethanol.

(5) Color reaction: Positive in iodine and anisaldehyde reactions.

(6) Visible absorption spectrum: As shown in FIG. 1 (82% methanol-water, v/v).

(7) Ultraviolet absorption spectrum: As shown in FIG. 2 (82% methanol-water, v/v).

(8) Infrared absorption spectrum: 3425, 2960, 2924, 2852, 1626, 1562, 1442, 1386, 1326, 1259, 1227, 1176, 1157, 1108, 1052, 1023 $cm^{-1}$ (KBr method).

(9) Mass spectrum: 382 (M+), 353, 334, 311, 308, 268.

(10) $^1$H-NMR spectrum (100 MHz, DMSO-$d_6$+$CD_3OD$, δ): 0.78 (3H, t, J=7.3), 1.67 (3H, br.d, J=5.9), ca. 1.7 (2H, m), 4.38 (2H, br.s), ca.5.1 (1H, m), 6.36 (1H, d, J=2.4), 6.93 (1H, d, J=2.4), 7.36 (1H, s).

(11) Molecular formula: $C_{21}H_{18}O_7$

(12) Molecular weight: 382

|  | H | C | N | O |
|---|---|---|---|---|
| Found: | 4.50 | 65.53 | 0 |  |
| Calculated ($C_{21}H_{18}O_7$) | 4.71 | 65.97 | 0 | 29.32 |

(14) Rf values obtained by silica gel thin layer chromatography are shown in the following Table 1:

TABLE 1

| Solvent system | Rf value* |
|---|---|
| 1. Chloroform/methanol/ethanol/water = 10:4:4:2 (v/v) | 0.56 |
| 2. n-butanol/ethanol/chloroform/ aqueous ammonium (28%) = 4:5:2:4 (v/v) | 0.35 |

*Thin layer . . . Kieselgel 60 (Art 5631, product of Merck AG., West Germany) Developed . . . room temperature, ascending, one hour. Detection was carried out by the irradiation of ultraviolet ray of 3650Å.

(15) For further investigation, a trimethyl derivative of K-259-2 substance was produced by treating with diazomethane by the method of Experiment 2 described hereinafter, which has the following characteristics:

(15-1) $^1$H-NMR spectrum (100 MHz, $CDCl_3$, δ): 0.85 (3H, t, J=6.6), 1.69 (3H, br.d, J=6.7), 1.5–1.9 (2H, m), 3.86 (3H, s), 3.92 (3H, s), 4.01 (3H, s), 4.21 (2H, br.s), ca. 5.3 (1H, m), 6.71 (1H, d, J=2.7), 7.31 (1H, d, J=2.7), 7.78 (1H, s), 13.06 (1H, s).

(15-2) $^{13}$C-NMR spectrum (25 MHz, $CDCl_3$, δc): 12.3; 13.6; 27.4; 32.8; 52.5; 56.0; 56.5; 106.7; 107.5; 108.1; 111.7; 117.8; 125.6; 132.0; 134.0; 137.5; 138.2; 144.1; 159.6; 165.3; 165.5; 167.1; 182.5; 188.1.

(15-3) Mass spectrum: m/z 424 (M+).

(15-4) Molecular formula: $C_{24}H_{24}O_7$ (15-5) Infrared absorption spectrum ($CCl_4$): 3440, 3096, 3016, 2968, 2936, 2876, 2860, 1739, 1672, 1627, 1575, 1485, 1463, 1442, 1386, 1368, 1316, 1250, 1228, 1210, 1192, 1165, 1142, 1108, 1077, 1039, 1022, 993, 954, 936, 930, 892, 867, 850, 740, 704, 646, 617 $cm^{-1}$.

With reference to the above-mentioned characteristics, it has been confirmed that K-259-2 is a new substance.

The acute toxity of K-259-2 substance is very low. With respect to its ability to dilate the artery of mammals and to its low toxity, K-259-2 is of interest in the provision of new vasodilator.

According to another feature of the present invention, there is provided a process for producing K-259-2 substance, which comprises culturing a microorganism of the genus Micromonospora capable of producing K-259-2 substance in a medium to accumulate the resultant K-259-2 substance in the cultured broth and recovering K-259-2 substance therefrom.

Any and all microorganisms of the genus Micromonospora capable of producing K-259-2 may be used for the purpose of the present invention. Preferred strains for this purpose include, for example, Micromonospora sp. K-259 (FERM BP 569) isolated from the soil at Nagaizumi-cho, Mishima-shi, Shizuoka-ken, Japan. This strain was filed with Bikoken (Fermentation Research Institute, Agency of Industrial Science and Technology, Japanese Government) on 18th July 1984 under the provisions of The Budapest Treaty.

K-259 strain has the following mycological characteristics.

Morphological characteristics:

This strain grows moderately on various organic media and the growth is moderate or poor on synthetic media. Aerial mycelium is not formed on all agar plate media. Vegetative mycelia colored in orange to dark green or black grow up on yeast extract-malt extract agar medium and Hickey-Tresner agar medium. Single spore is formed at the top end of simply branched vegetative mycelium, which is spherical and has a diameter of about 0.7–0.9 micron. When observed by electronic miscroscope, the surface of the spore is warty and both flagellum and sporangium are not found.. Brownish soluble pigment is not found except on yeast extract-malt extract agar medium.

Cultural characteristics on various media:

The following cultural characteristics were obtained by culturing the strain at 28° C. for 2 weeks on each occasion. Color name and hue number are expressed by referring to the classification shown in Color Harmony Manual edited by Container Corporation of America.

When cultured by using the following media, no aerial mycelium was formed. Soluble pigment was not produced except on yeast-extract-malt extract agar medium.

In the following cultural characteristics, G, S and R denote respectively the growth, the surface and the reverse, and ISP denote the medium recommended by International Streptomyces Project.

(1) Sucrose-nitrate-agar medium:
  G . . . moderate; S and R . . . black (17 pn)
(2) Glucose-asparagine-agar medium:
  G . . . poor; S and R . . . black (19 pn)
(3) Glycerol-asparagine-agar medium (ISP No. 5):
  G . . . poor; S and R . . . black olive (1 po)
(4) Starch-agar-medium (ISP No. 4)
  G . . . poor to moderate; S and R . . . bright orange (4 ga)
(5) Tyrosine-agar medium (ISP No. 7)
  G . . . poor; S and R . . . black (15 po)
(6) Nutrient-agar medium
  G . . . poor; S and R . . . copper (5 lc) to dark bottle green (22 pn)
(7) Yeast extract-malt extract-agar medium
  G . . . good (raised); S and R . . . black (15 po);
  Soluble pigment . . . mustard brown (2 pl)
(8) Oatmeal-agar medium
  G . . . moderate; S and R . . . burnt orange (5 nc)
(9) Hickey-Tresner agar medium
  G . . . good (raised); S and R . . . golden brown (4 pi) to black (18 pn)
(10) Peptone-yeast extract-iron agar medium
  G . . . moderate; S and R . . . amber (4 pe)

Physiological characteristics:

The strain was cultured at 28° C. for 3 weeks and then the following characteristics were determined with the exception that the growth temperature and the activity upon skim milk and cellulose were respectively determined 2 days and one month after the beginning of culturing.

(1) Utilization of carbon sources:
  Positive
  D-glucose, L-arabinose, D-xylose, D-fructose, L-rahmnose, sucrose and melibiose
  Negative:
  i-inositol, D-mannitol and raffinose
(2) Liquefaction of gelatin: negative
(3) Coagulation of skim milk and peptonization: positive
(4) Decomposition of cellulose: positive
(5) Hydrolysis of starch: positive
(6) Growth temperature range:
  18°–33° C., optimal range 26°–30° C.
(7) Formation of melanoid pigment: negative.

Strain K-259 is mesophilic. No aerial mycelium is formed. Single spore is formed at the top end of simply branched vegetative mycelium. Fragmentation of mycelium is not found. Analysis of the cell wall indicates the presence of 2,6-diamino-3-hydroxy-pimelic acid. Analysis of sugars in the whole cells indicates the presence of xylose and arabinose. From these facts, it has been found that this strain may be classified into the genus Micromonospora of the order Actinomycetales.

Strain K-259 may be cultured in a conventional manner used for culturing strains of Actinomyces. Thus, any synthetic or organic medium may be used for culturing the strain of the present invention when it contains suitable amounts of an assimilable carbon source, nitrogen source, inorganic substances and the like.

By way of examples, it is preferred to use as the carbon source, glucose, fructose, sucrose, starch, dextrin, mannit, maltose, molasses and other carbohydrates, citric acid, malic acid, acetic acid, fumaric acid and other organic acids, methanol, ethanol and other alcohols, methane, ethane, propane, n-paraffin and other hydrocarbons, glutamic acid and other amino acids and glycerol.

The nitrogen sources which may be used for the purpose of the present invention are exemplified by ammonium salts of chloric, sulfuric, nitric and phosphoric acids; aspartic acid, glutamine, cystine, alanine and other amino acids; urea, peptone, meat extract, yeast extract, dried yeast, corn steep liquor, soybean powder, cotton seed cake, soybean casein, cazamino acid, Pharmamedia and the like.

Preferred inorganic substances which may be used for the purpose of the present invention include, for example, potassium dihydrogenphosphate, sodium dihydrogenphosphate, magnesium sulfate, ferrous sulfate, manganese sulfate, cobalt sulfate, zinc sulfate, calcium pantothenate, ammonium molybdate, aluminium potassium sulfate, barium carbonate, calcium carbonate, cobalt chloride, sodium chloride and the like.

If desired, it is possible to add to the medium, for example, vitamins, thiamine and various other substances capable of promoting the growth of strain K-259 and/or promoting the production of K-259-2 substance. When an auxotrophic strain is cultured, it is necessary to supplement the medium with a suitable nutrient required for the growth of the strain used.

The fermentation may be usually effected under aerobic conditions, for example, by shaking or shaking with aeration at a temperature of 20°–40° C. and at a neutral pH. Culturing is usually discontinued when the concentration of K-259-2 substance reaches maximum, for example, 3–15 days after the beginning of culturing.

K-259-2 substance may be isolated from the cultured broth in a conventional manner used for isolating various known physiologically active substances from a cultured broth. Thus, the isolation of K-259-2 substance may be effected, for example, by removal of cells by filtration, centrifugation and the like, followed by adsorption of the active substance by column chromatography or thin layer chromatography and the like using, for example, adsorbing resins, silica gel, Silanized Silicagel (product of Merck AG., West Germany), aluminium, cellulose, diatomaceous earth, magnesium silicate, gel filtration agents and the like.

K-259-2 may be isolated from the cultured broth, for example, in the following manner.

The cells are removed from the cultured broth, for example, by filtration or centrifugation. The resultant filtrate or supernatant is treated, for example, with an adsorbing resin such as Diaion HP-10 (Mitsubishi Kasei Kogyo K.K., Japan) to adsorb the active material onto the resin. The active material is eluted with a suitable solvent such as, for example, methanol, followed by removal of the solvent by evaporation under reduced pressure. To the resultant aqueous solution containing the active material is added a suitable solvent such as, for example, ethyl acetate, butyl acetate and the like, which is not miscible with water to extract the active material.

The extracted solution is concentrated under reduced pressure and then purified by repeating silica gel column chromatography. In this case, for example, a solvent system of butanol/ethanol/chloroform/concentrated aqueous ammonium (4:5:2:4 v/v) may be used, followed by the use of a solvent system of, for example, chloroform/methanol/ethanol/water (10:4:4:2 v/v). The eluted fractions containing K-259-2 substance are collected, combined and concentrated under reduced pressure. The concentrated solution is subjected to chromatography using, for example, Sephadex LH-20 (Pharmacia Fine Chemicals AB., Sweden) and elution is carried out using methanol. The eluate is collected, combined and treated by silica gel chromatography using, for example, a solvent system of chloroform/methanol/ ethanol/water (10:4:4:2 v/v). The eluted fractions containing K-259-2 substance are collected, combined and concentrated under reduced pressure. The concentrated solution is subjected to reverse phase silica gel chromatography, for example, using a solvent system of methanol/water (7:3 v/v). The eluate is collected, combined and concentrated under reduced pressure to obtain crude powders of K-259-2 substance. The crude product may be purified by recrystallization using a suitable solvent such as, for example, methanol, water and the like to obtain needle crystals of K-259-2 substance.

The present invention further provides a pharmaceutical composition comprising an effective amount of K-259-2 substance.

The composition according to the present invention may be in any form conventionally used in the pharmaceutical art, for example, emulsions, hydrates, solutions, powders, granules, capsules or tablets.

The composition may contain suitable additives such as, for example, various excipients, disintegrators, lubricants, binders, dispersants and plasticizers conventionally used in the pharmaceutical art.

Suitable excipients which may be used for the purpose of the present invention include, for example, lactose, glucose, sucrose, dextrose, sorbitol, mannitol, gelatin, arabic gum and the like. Suitable disintegrators include, for example, starch, sodium alginate, agar powders and calcium carboxymethylcellulose. Suitable lubricants are exemplified by magnesium stearate, talc, vegetable oil, and liquid paraffin. Suitable binders include, for example, simple syrup, gelatin solution, ethanol and polyvinyl alcohol. Suitable dispersants include, for example, methylcellulose, ethylcellulose, hydroxypropyl cellulose and shellac. Suitable plasticizers include, for example, glycerol and starch.

The composition may be prepared by conventional methods of pharmacy. The amount of the active ingredient in the composition may widely vary, depending upon the form and purpose of the composition and may be, for example, 0.01–85% by weight of the composition.

The administration of compositions of the present invention may be effected by conventional procedures used in the pharmaceutical art, for example, parenterally (intravenously or subcutaneously), topically or orally. Preferred compositions are in unit dosage form. Thus, it is possible to administer a composition of the present invention, for example, by intravenous injection, at a daily dose of from about 0.1–4.0 mg/kg of body weight (on the basis of the active ingredient). Usually, a dose of about 5–10 fold greater amount may be used for oral administration as compared to the dosage for intravenous injection. However, the preferred dose may vary considerably, depending upon the type of patient (age, condition, etc).

The following non-limiting example illustrates the invention.

EXAMPLE

Micromonospora sp. K-259 (FERM BP 569) was inoculated to a first seed medium (40 ml) containing glucose (1.0g/dl), soluble starch (1.0 g/dl), meat extract (0.3 g/dl), yeast extract (0.5 g/dl), Bactotryptone, Difco., U.S.A. (0.5 g/dl) and calcium carbonate (0.2 g/dl) (pH 7.2–7.4) put in an Erlenmeyer flask (300 ml). Culturing was effected with shaking at 30° C. for a period of time sufficient for growth of the strain. 40 ml of the resultant seed was inoculated to a second seed medium (400 ml) having the same composition as that described above put in a 2 l Erlenmeyer flask for culturing with shaking at 28° C. for 3 days. The resultant seed (1.2 l) was transferred to 18 l of a fermentation medium put in a 30 l jar fermentor, the fermentation medium having the following composition:

Glucose 0.5 g/dl; soluble starch 3.0 g/dl; soybean powders 3.0 g/dl; corn steep liquor 0.5 g/dl; yeast extract 0.5 g/dl; calcium carbonate 0.3 g/dl(pH 7.2–7.4).

Culturing was effected with aeration and shaking at 30° C. for 4 days to accumulate 5 $\mu$g/ml of K-259-2 substance in the cultured broth. After completion of culturing, the cultured broth was continuously centrifuged (15,000 r.p.m) to obtain a supernatant, of which 70 l was transferred to a column (2 l) packed with Diaion HP-10 to adsorb K-259-2 substance, followed by washing with methanol (30%, 6 l). A further elution was effected with methanol (6 l). The eluted fractions were collected, combined and concentrated to 500 ml. After adjusting the pH to 2.0 with 2N hydrochloric acid, extraction was effected with ethyl acetate (1.5 l). The ethyl acetate layer was treated with anhydrous sodium sulfate and concentrated to dryness to result in an oily material (18 g). The oily material was transferred to a column packed with silica gel (2 l; Wako gel, Wako Junyaku K.K.) equilibrated with a solvent system of butanol/ethanol/ chloroform/concentrated aqueous ammonium (4:5:2:4 v/v). Elution was effected with the same solvent system as that described above. The eluate was divided into fractions (each 18 g). The active material was present in Fraction Nos. 40–75 which were combined and concentrated to dryness under reduced pressure to result in an oily material (about 4.0 g).

This oily material was transferred to a column packed with silica gel (1 l; Wako gel) equilibrated with a solvent system of chloroform/methanol/ethanol/water (10:4:4:2 v/v). Elution was effected with a same solvent system as that described above. The eluate was divided into fractions (each 18 g). K-259-2 substance was present in Fraction Nos. 12–40, which were combined and concentrated to dryness under reduced pressure to result in an oily material (about 200 mg). The oily material was dissolved in methanol (5 ml) and transferred to a column packed with Sephadex LH-20 (200 ml; Pharmacia Fine Chemicals AB., Sweden). Methanol was used for elution. The eluate was divided into small fractions (each 10 g). K-259-2 substance was present in Fraction Nos. 18–44, which were combined and concentrated to dryness under reduced pressure to result in an oily material (about 60 mg). The oily material was transferred to a column packed with 100 ml of silica gel (Wako gel) equilibrated with a solvent system of chloroform/methanol/ ethanol/water (10:4:4:2 v/v). Elution was effected by using the same solvent system as that described above. The eluate was divided into fractions (each 5 g). K-259-2 substance was present in Fraction Nos. 5–26, which were collected, combined and concentrated under reduced pressure to result in reddish brown powders (about 30 mg). The powders were dissolved in methanol (about 3 ml) and adsorbed onto Silanized Silica-gel RP-8 (size B, Art 11804, product of Merck AG. West Germany) equilibrated with a solvent system of methanol/water (7:3 v/v). Elution was effected with the same solvent system as that described above. The eluate was divided into fractions (each 10 g). K-259-2 substance was present in Fraction Nos. 30–64, which were then combined and concentrated to dryness under reduced pressure to result in red powders (about 25 mg). The powders were dissolved in methanol (about 5 ml). After addition of water (3 ml), the solution was allowed to stand at 5° C. for a period of about 7 days to result in red needle crystals (21 mg).

In the above-mentioned purifying step, K-259-2 substance was assayed by means of silica gel thin layer chromatography, followed by either the iodine reaction or the visualization under ultraviolet ray (3650 Å).

The following Experiment 1 indicates the vasodilating activity of K-259-2 substance, in which an artery sample taken out from animal was used to show the inhibition of the contraction of artery by action of K-259-2 substance. Experiment 2 indicates the preparation of the trimethyl derivative of K-259-2.

EXPERIMENT 1

(1) A sample of artery prepared by surface perfusion of the superior mesenteric artery excised from rabbit:

By a mid-line incision over the abdominal region, the superior mesenteric artery having a length of about 2–2.5 cm was cut out from the branch of the abdominal aorta of a mongrel rabbit(male; body weight 2–3 kg) to prepare a sample of artery in the form of a spiral having a width of 3–4 mm. The sample was ligated with silk threads at the both ends. The lower end was attached to a stationary bar and the upper end was connected to a high performance transducer (SB-1T, Nihon Koden K.K., Japan). The sample was hung down with an initial tension of 1.5 g. A peristaltic pump (Harbard 1210) was used to keep the sample at 36°–38° C. in an atmosphere of 95% oxygen containing 5% carbon dioxide. Surface perfusion of the sample was effected at a rate of 10 ml/min by the use of Krebs-Henseleit solution composed of NaCl (6.92 g/l), KCl (0.35 g/l), $MgSO_4:7H_2O$ (0.29 g/l), $CaCl_2$ (0.28 g/l), $KH_2PO_4$ (0.16 g/l), $NaHCO_3$ (2.1 g/l) and glucose (2.0 g/l).

After being stabilized for a period of 1–2 hours, the sample was used for experiment in the following manner.

Potassium chloride was used as a vaso-constrictor at a final concentration of 20 mM. It was supplied to the perfusion tubing from a canule retained very near the sample. The contractile reaction induced by surface perfusion was recorded on a polygraph (RM-45, Nihon Koden K.K., Japan) via the tension transducer substantially in the natural scale.

K-259-2 substance was dissolved in ethanol at a final concentration of 20 mg/ml, and the solution was suitably diluted with a nutrient solution to prepare sample solutions of K-259-2 substance. On each occasion, the administration of the sample solution was started 10 minutes before the beginning of the experiment and continued during the experiment.

(2) The results are shown in Table 2.

TABLE 2

| Constrictor | Concentration of K-259-2* | Contractile Inhibition (%)** |
|---|---|---|
| Potassium chloride 20 mM | 3 | 15.4 |
|  | 10 | 45.5 |

Notes:
*Final concentration (μg/ml)
**Inhibition rate (%) = (1-A/B) × 100
A = contractile rate in the presence of K-259-2
B = contractile rate in the absence of K-259-2

It has been found that K-259-2 substance is capable of inhibiting the contraction of the mesenteric artery of a rabbit and its activity is proportional to its concentration. Thus, this substance is of interest in providing a vasodilator for humans and mammals.

EXPERIMENT 2

In this experiment, 45 mg of K-259-2 substance obtained in Example was dissolved in 5 ml of ethyl acetate. 2 ml of diazomethane ether solution was added and the mixture was stirred at room temperature for 0.5 hour. The solution was evaporated in vacuo and subjected to silica gel column chromatography. Elution was carried out using a solvent system of n-hexane/ethyl acetate (4:1 v/v). Fractions containing trimetyl derivative of K-259-2 substance were combined and concentrated in vacuo to obtain 38 mg of trimethyl derivative of K-259-2 substance having the physical characteristics as previously described.

We claim:

1. A substance K-259-2 having the following physicochemical characteristics:
   (1) Nature: Reddish needle crystal. Alkaline substance.

(2) Melting point:

140°–145° C. (decomp.). Becomes brownish at a temperature of more than about 140° C. Melting point indefinite.

(3) Specific rotation:

$[\alpha]_D^{20} = 0°(c=0.33, CH_3OH)$ (4) Solubility:

Readily soluble in acetic acid, soluble in methanol and water, and hardly soluble in chloroform, ethyl acetate, acetone and ethanol.

(5) Color reaction:

Positive in iodine and anisaldehyde reactions.

Figure 1:
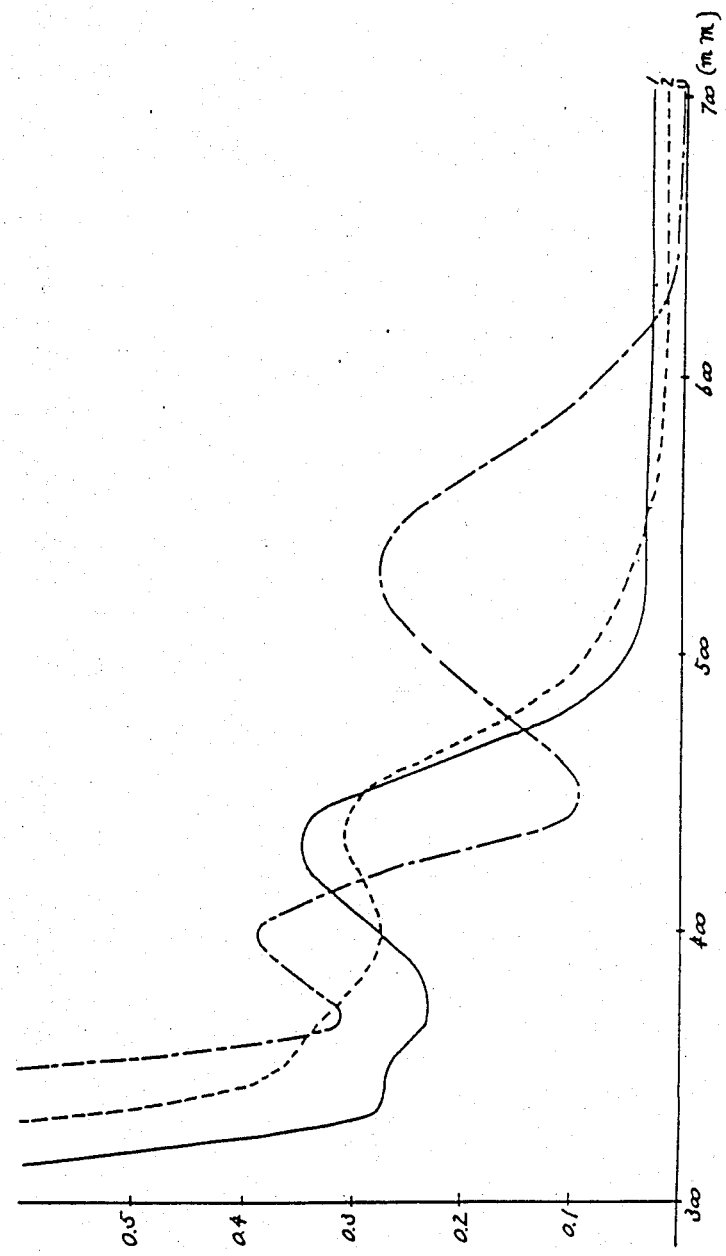
FIG. 1 shows the visible absorption spectrum of K-259-2 substance, in which lines (1), (2) and (3) denote respectively the results obtained by the use of 0.1 N HCl/82% (v/v) aqueous methanol; 82% (v/v) aqueous methanol and 0.1 N NaOH/82% (v/v) aqueous methanol.

(6) Visible absorption spectrum:

As shown in FIG. 1 (82% methanol-water, v/v)

Figure 2:
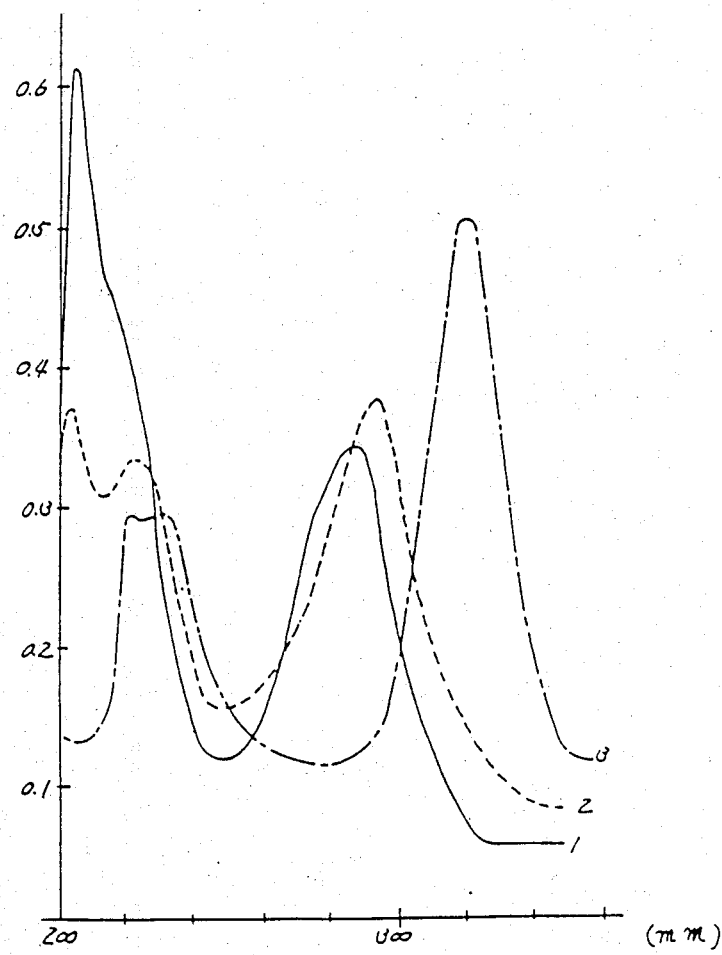
FIG. 2 shows the ultraviolet absorption spectrum of K-259-2 substance, in which lines (1) to (3) are as hereinbefore defined.

(7) Ultraviolet absorption spectrum:

As shown in FIG. 2 (82% methanol-water, v/v)

(8) Infrared absorption spectrum:

3425, 2960, 2924, 2852, 1626, 1562, 1442, 1386, 1326, 1259, 1227, 1176, 1157, 1108, 1052, 1023 $cm^{-1}$
(KBr method)

(9) Mass spectrum:

382 ($M^+$), 353, 334, 311, 308, 268.

(10) $^1H$-NMR spectrum (100 MHz, DMSO-$d_6$+$CD_3OD$, $\delta$):

0.78 (3H, t, J=7.3), 1.67 (3H, br.d, J=5.9), ca. 1.7 (2H, m), 4.38 (2H, br.s), ca. 5.1 (1H, m), 6.36 (1H, d, J=2.4), 6.93 (1H, d, J=2.4), 7.36 (1H, s).

(11) Molecular formula: $C_{21}H_{18}O_7$

(12) Molecular weight: 382

|  | H | C | N | O |
|---|---|---|---|---|
| Found: | 4.50 | 65.53 | 0 |  |
| Calculated ($C_{21}H_{18}O_7$) | 4.71 | 65.97 | 0 | 29.32 |

(14) Rf values obtained by silica gel thin layer chromatography:

| Solvent system | Rf value* |
|---|---|
| 1. Chloroform/methanol/ethanol/water = 10:4:4:2 (v/v) | 0.56 |
| n-butanol/ethanol/chloroform/aqueous ammonium (28%) = 4:5:2:4 (v/v) | 0.35 |

*Thin layer . . . Kieselgel 60 (Art 5631, product of Merck AG., West Germany)

2. A process for producing a substance K-259-2 as defined in claim 1, which comprises culturing for 3 to 15 days under anaerobic conditions at a temperature of 20° to 40° C. and at a neutral pH the microorganism Micromonospora sp. K-259 (FERM BP569) in a medium so as to accumulate substance K-259-2 in the cultured broth and recovering the resultant the substance K-259-2 therefrom.

3. A vasodilating composition for humans and veternary use, comprising an effective amount sufficient for vasodilation of substance K-259-2 as claimed in claim 1, in association with a physiologically acceptable carrier or excipient.

4. The composition of claim 4 in the form of a daily dosage of 0.1 to 4.0 mg of K-259-2 per kg of body weight.

5. A process for dilating the blood vessels of an animal subject which comprises administering substance K-259-2 of claim 1 in association with a physiologically accepted carrier or excipient at a daily dosage of from 0.1 to 4.0 mg. of K-259-2 per kg. of body weight of animal subject.

* * * * *